United States Patent
Lee et al.

(10) Patent No.: US 6,284,795 B1
(45) Date of Patent: Sep. 4, 2001

(54) SULFONAMIDE COMPOUNDS AND METHODS OF TREATING ATHEROSCLEROSIS AND RESTENOSIS

(75) Inventors: Helen Tsenwhei Lee; Randy Ranjee Ramharack, both of Ann Arbor; Bruce David Roth, Plymouth; Karen Elaine Sexton, Ann Arbor, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/376,268

(22) Filed: Aug. 18, 1999

Related U.S. Application Data

(60) Provisional application No. 60/099,180, filed on Sep. 4, 1998.

(51) Int. Cl.[7] .................. A61K 31/18; C07C 303/36; C07C 303/38; C07D 409/06
(52) U.S. Cl. .............. 514/604; 514/605; 564/81; 564/89; 564/90; 564/92; 564/96; 564/97; 564/98; 546/280.4
(58) Field of Search ................... 514/604, 605; 564/89, 96, 98, 81, 90, 92, 97

(56) References Cited

U.S. PATENT DOCUMENTS

| | | | |
|---|---|---|---|
| 4,535,165 | 8/1985 | Moore et al. | 548/204 |
| 5,234,939 | 8/1993 | Capris et al. | 514/400 |
| 5,489,611 | 2/1996 | Lee et al. | 514/557 |
| 5,491,172 | 2/1996 | Lee et al. | 514/602 |

FOREIGN PATENT DOCUMENTS

| | | | |
|---|---|---|---|
| 617001 | * | 9/1994 | (EP) . |
| 95/21151 | | 8/1995 | (WO) . |
| 96/08487 | | 3/1996 | (WO) . |
| 96/09818 | | 4/1996 | (WO) . |
| 97/02037 | | 1/1997 | (WO) . |
| 97/02266 | * | 1/1997 | (WO) . |
| 97/05095 | | 2/1997 | (WO) . |

OTHER PUBLICATIONS

Isomura, et al., *Chem. Pharm. Bull.*, "Synthesis and Anti–inflammatory Activity of 2,6–Di–tert–butylphenols with a Heterocyclic Group at the 4–Z position. III", 1984, vol. 32:1, pp. 152–165.

Lazer, et al., *J. Med. Chem.*, "Antinnflammatory 2,6–Di–tert–butyl–4–(2–arlethenl)phenos", 1989, vol. 32, pp 100–104.

* cited by examiner

*Primary Examiner*—Alan L. Rotman
(74) *Attorney, Agent, or Firm*—Charles W. Ashbrook

(57) ABSTRACT

The present invention provides compounds having the Formula I

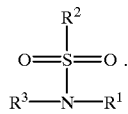

I

The present invention also provides methods of treating or preventing atherosclerosis, coronary heart disease, and restenosis using the compounds of Formula I, and pharmaceutical compositions comprising the compounds of Formula I.

16 Claims, No Drawings

SULFONAMIDE COMPOUNDS AND METHODS OF TREATING ATHEROSCLEROSIS AND RESTENOSIS

This application claims the benefit of provisional application Ser. No. 60/099,180, filed Sep. 4, 1998.

FIELD OF THE INVENTION

The present invention relates to compounds that are sulfonamides, and to methods of treating atherosclerosis, coronary heart disease, and restenosis using the sulfonamide compounds. The invention also relates to a pharmaceutical composition that comprises a sulfonamide of the present invention.

BACKGROUND OF THE INVENTION

Vascular diseases such as coronary heart disease, atherosclerosis, stroke, restenosis, and peripheral vascular disease, remain the leading cause of death and disability throughout the world. About 1.5 million people die each year in the United States alone from myocardial infarction resulting from congestive heart failure. While diet and life style can accelerate the onset of vascular diseases, genetic predisposition leading to dyslipidemia is a significant factor in vascular-related disabilities and deaths. "Dyslipidemia" means abnormal levels of lipoproteins in blood plasma.

Several risk factors have been associated with increased risk of vascular disease. Among these are the dyslipidemias of high levels of low-density lipoprotein (LDL), and low levels of high-density lipoproteins (HDL). The ratio of HDL- to LDL-cholesterol is often used to assess the risk of vascular disease. A high ratio of HDL/LDL cholesterol is desirable. Compounds that increase this ratio by either lowering LDL or increasing HDL, or both, therefore are beneficial. Recent studies have also shown that elevated levels of lipoprotein(a), "Lp(a)", are detrimental.

Lp(a) appears to be undesirable, since elevated levels of Lp(a) have been associated with the development of atherosclerosis, coronary heart disease, myocardial infarction, stroke, cerebral infarction, and restenosis following balloon angioplasty. In fact, Lp(a) appears to be an excellent predictor for stroke. Accordingly, a high concentration of Lp(a) is one of the major risk factors leading to death from heart disease.

Lp(a) is composed of LDL and a high molecular weight glycoprotein called apolipoprotein(a), apo(a). Epidemiological studies show that, when present in high levels in the plasma, Lp(a) is an independent risk factor for premature atherosclerotic coronary heart disease. A concentration of 0.30 g/L in plasma is considered to double the risk of premature coronary heart disease. This concentration has been used as a clinical set point to determine what plasma concentrations of Lp(a) are considered above normal and for which treatment to lower plasma Lp(a) levels may be desirable.

SUMMARY OF THE INVENTION

The present invention provides compounds of the Formula I

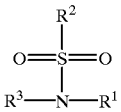

wherein $R^1$ is heteroaryl, substituted heteroaryl, —$(CH_2)_n$-$C_3$-$C_8$ cycloalkyl, —$(CH_2)_n$-aryl, or —$(CH_2)_n$-substituted aryl;

$R^2$ is $C_1$-$C_6$ alkyl, heteroaryl, substituted heteroaryl, aryl, substituted aryl, or

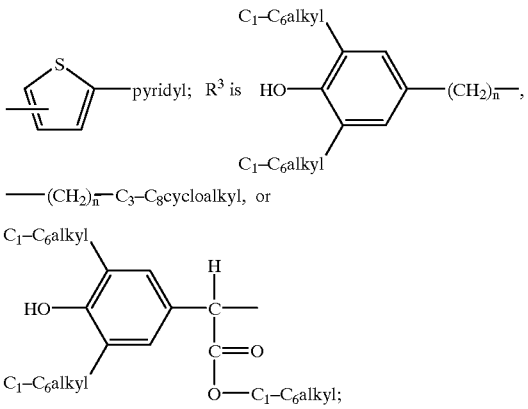

n is 0 to 4, and the pharmaceutically acceptable salts thereof.

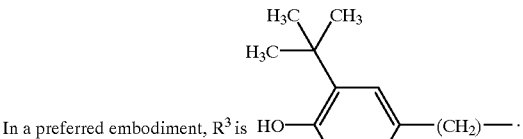

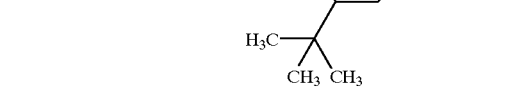

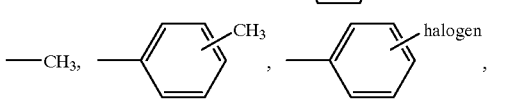

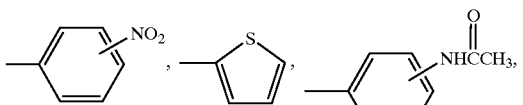

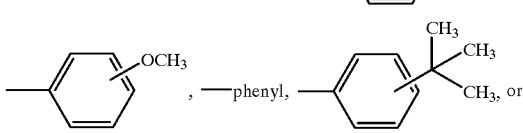

-continued

—CH₂—phenyl, or 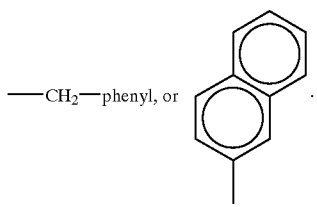

In a preferred embodiment, $R^1$ is pyridyl, —CH₂-cyclohexyl,

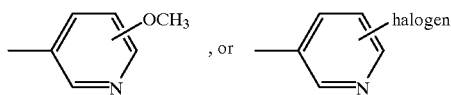

In a more preferred embodiment, the present invention provides compounds of the Formula I

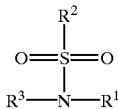    I wherein
$R^1$ is pyridyl, —CH₂ cyclohexyl, or -substituted pyridyl;
$R^2$ is -thienyl-pyridyl, —$C_1$-$C_6$ alkyl, substituted phenyl, thienyl, or —CH₂-phenyl;

$R^3$ is 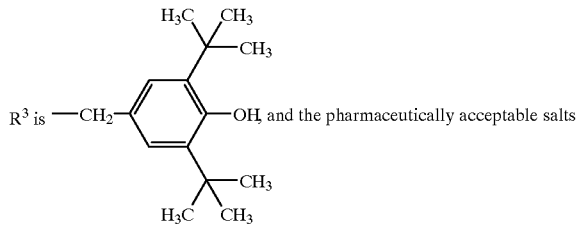 and the pharmaceutically acceptable salts thereof.

In a most preferred embodiment, the present invention provides the compounds:

5-Pyridin-2-yl-thiophene-2-sulfonic acid (3,5-di-tert-butyl-4-hydroxy-benzyl)-pyridin-3-yl-amide;

(Cyclohexylmethyl-methanesulfonyl-amino)-(3,5-di-tert-butyl-4-hydroxy-phenyl)-acetic acid ethyl ester;

N-(3,5-Di-tert-butyl-4-hydroxy-benzyl)-4-methyl-N-pyridin-3-yl-benzenesulfonamide;

N-(3,5-Di-tert-butyl-4-hydroxy-benzyl)-4-fluoro-N-pyridin-3-yl-benzenesulfonamide;

N-(3,5-Di-tert-butyl-4-hydroxy-benzyl)-4-nitro-N-pyridin-3-yl-benzenesulfonamide;

Thiophene-2-sulfonic acid (3,5-di-tert-butyl-4-hydroxy-benzyl)-6-methoxy-pyridin-3-yl-amide;

Thiophene-2-sulfonic acid (3,5-di-tert-butyl-4-hydroxy-benzyl)-pyridin-3-yl-amide;

N-(3,5-Di-tert-butyl-4-hydroxy-benzyl)-4-acetamido-N-pyridin-3-yl-benzenesulfonamide;

N-(3,5-Di-tert-butyl-4-hydroxy-benzyl)-4-methoxy-N-pyridin-3-yl-benzenesulfonamide;

N-(3,5-Di-tert-butyl-4-hydroxy-benzyl)-3-nitro-N-pyridin-3-yl-benzenesulfonamide;

N-(3,5-Di-tert-butyl-4-hydroxy-benzyl)-3-N-pyridin-3-yl-benzenesulfonamide;

N-(3,5-Di-tert-butyl-4-hydroxy-benzyl)-N-pyridin-3-yl-methanesulfonamide;

N-(2-Chloro-pyridin-3-yl)-N-(3,5-di-tert-butyl-4-hydroxy-benzyl)-4-methyl-benzenesulfonamide;

N-(3,5-di-tert-butyl4-hydroxybenzyl)-2-bromo-N-pyridin-3-yl-benzenesulfonamide;

N-(6-Chloro-pyridin-3-yl)-N-(3,5-di-tert-butyl-4-hydroxybenzyl)-4-methyl-benzenesulfonamide;

N-(3,5-di-tert-butyl-4-hydroxybenzyl)-2-naphthalene-N-pyridin-3-yl-sulfonamide;

N-(3,5-di-tert-butyl-4-hydroxy-benzyl)-N-(6-methoxy-pyridin-3-yl)-4-methyl-benzenesulfonamide; and N-(3,5-di-tert-butyl-4-hydroxybenzyl)-3-bromo-N-pyridin-3-yl-benzenesulfonamide.

Also provided is a pharmaceutical composition comprising a compound of Formula 1.

Also provided is a method of lowering plasma Lp(a) in a patient, the method comprising administering to a patient in need of Lp(a) lowering a therapeutically effective amount of a compound of Formula I.

Also provided is a method of treating or preventing atherosclerosis, the method comprising administering to a patient having or at risk of having atherosclerosis a therapeutically effective amount of a compound of Formula I.

Also provided is a method of treating coronary heart disease, the method comprising administering to a patient having coronary heart disease a therapeutically effective amount of a compound of Formula I.

Also provided is a method of treating or preventing restenosis, the method comprising administering to a patient having restenosis or at risk of having restenosis a therapeutically effective amount of a compound of Formula I.

DETAILED DESCRIPTION OF THE INVENTION

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl.

The term "aryl" means an aromatic ring such as phenyl, 5-fluorenyl, 1-naphthyl, or 2-naphthyl group, unsubstituted or substituted by 1 to 3 substituents which can be selected from, but not limited to, —$C_1$-$C_6$ alkyl, —O—C-$C_6$ alkyl, and —S—$C_1$-$C_6$ alkyl, —OH, —SH, —F, —CN, —Cl, —Br, —I, —CF₃, —NO₂, —CO₂H, —CO₂$C_1$-$C_6$ alkyl, —NH₂, —NHC₁-$C_6$ alkyl, N($C_1$-$C_6$alkyl)₂, or

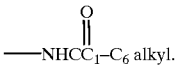
—NHCC₁-C₆ alkyl.

The term "heteroaryl" means an aromatic ring containing one or more heteroatoms. Examples of heteroaryl radicals include thienyl, furyl, pyrrolyl, pyridyl, imidazolyl, or indolyl group, substituted or unsubstituted by 1 or 2 substituents from the group of substituents described above for aryl. Examples of heteroatoms include nitrogen, oxygen, sulfur, and phosphorus.

The term "cycloalkyl" means a saturated hydrocarbon ring which contains from 3 to 7 carbon atoms, and includes for example, cyclopropyl, cyclobutyl, cyclopentyl, cyclohexyl, adamantyl, and the like. The cycloalkyl group can be substituted with from 1 to 3 substituents from the group of substituents described above for aryl.

The symbol "—" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of or prevents atherosclerosis, coronary heart disease, or restenosis, or lowers plasma levels of Lp(a). A therapeutically effective amount of a compound of the present invention can be easily determined by one skilled in the art by administering a quantity of a compound to a patient and observing the result. In addition, those skilled in the art are familiar with identifying patients having restenosis, coronary heart disease, or atherosclerosis or who are at risk of having restenosis, coronary heart disease, or atherosclerosis.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.,* 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can be synthesized using standard organic methodology, including combinatorial chemistry or by biological processes such as through metabolism. It is intended that the present invention include compound made by any process.

The examples presented below are intended to illustrate particular embodiments of the invention, and are not intended to limit the scope of the specification or the claims in any way.

EXAMPLES

General Synthesis

The compounds of the present invention can be synthesized in general as follows with reference to Scheme 1.

A mixture of a substituted aldehyde (1) and a substituted amine (2) together with catalytic amount of p-toluene sulfonic acid are refluxed in toluene for 20 hours, the toluene is removed, and pure imine (3) is isolated by recrystallization. The isolated imine is hydrogenated under $H_2$ to generate an amine (4). The final product (6) is obtained by sulfonylation between the amine (4) and the substituted sulfonyl chloride (5) in pyridine.

Scheme 1

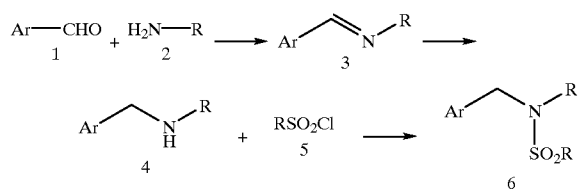

EXAMPLE 1

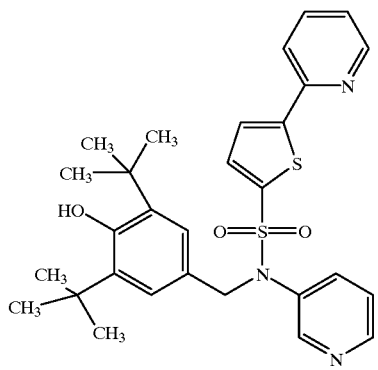

5-Pyridin-2-yl-thiophene-2-sulfonic acid (3,5-di-tert-butyl-4-hydroxy-benzyl)-pyridin-3-yl-amide This compound was prepared in the same manner as for the title compound of Example 7, except the 2-thiophene sulfonyl chloride was replaced with 5-pyridin-2-yl-thiophene-2-sulfonyl chloride.

Elemental Analysis $C_{29}H_{33}N_3S_2O_3 \cdot 1.5\ H_2O$: Calculated: C, 61.89; H, 6.40; N, 7.46. Found: C, 62.23; H, 6.36.3; N, 7.46. MS (APCI/M+1)=536.3

EXAMPLE 2

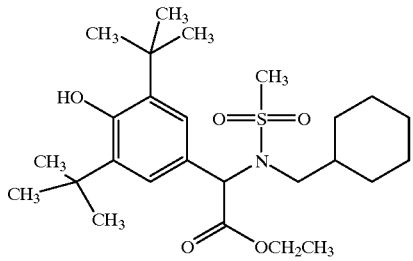

(Cyclohexylmethyl-methanesulfonyl-amino)-(3,5-Di-tert-butyl-4-hydroxy-phenyl)-acetic acid ethyl ester To a solution of 3,5-di-tert-butyl-4-hydroxyphenyl acetic acid (8 g, 30.3 mmol) in ethanol (60 mL) was added HCl gas until the solution was saturated. The reaction was stirred overnight at room temperature. The mixture was evaporated in vacuo, taken up in EtOAc, washed with water and brine, dried over magnesium sulfate and concentrated to give the ester as an oil.

To the ester (3.25 g, 11.1 mmol, 1 eq) in carbon tetrachloride (25 mL) was added N-bromosuccinimide (3.0 g, 16.6 mmol, 1.5 eq) and benzoyl peroxide (3 mg). The reaction was warmed to 60° C. overnight. The reaction was cooled, concentrated in vacuo, taken up in $Et_2O$ and washed with water, dried over magnesium sulfate and concentrated in vacuo to give the brominated product as an orange oil.

The solution of brominated ester (1 eq) in THF was added cyclohexanemethyl amine (2.1 eq). The reaction was stirred at room temperature for 1 hour. The solvent was removed in vacuo. The residue was taken up in EtOAc, washed with brine, dried over magnesium sulfate, filtered and concentrated. The crude product was chromatographed on silica gel eluting with a gradient of EtOAc/hexane.

To a solution of the amino acid (1 eq) in EtOAc was added methanesulfonyl chloride (2 eq) and triethylamine (2.7 eq). Stirred at room temperature for 2 hours. The reaction was washed with water and brine, dried over magnesium sulfate, filtered and concentrated. The crude product was chromatographed on silica gel eluting with 2% MeOH/$CH_2Cl_2$. The solid was recrystallized from hexanes/pentane and dried in vacuo at 60° C. (21%)

Mp: 164° C.; Elemental Analysis: $C_{26}H_{43}NO_5S$ Calculated: C, 64.83; H, 9.00; N, 2.91 Found: C, 64.93; H, 8.92; N, 2.88

EXAMPLE 3

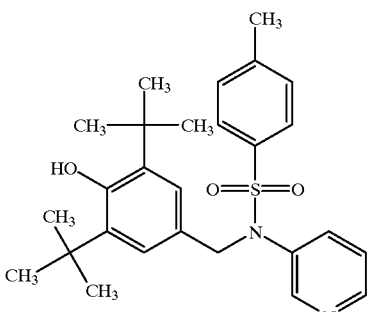

N-(3,5-Di-tert-butyl-4-hydroxy-benzyl)-4-methyl-N-pyridin-3-yl-benzenesulfonamide The procedure for Example 7 was followed using p-toluenesulfonyl chloride. The reaction was stirred at 60° C. for 17 hours. The crude product was chromatographed on silica gel eluting with 40% EtOAc/hexanes and then recrystallized from EtOAc/hexanes to obtain desired compound (52%).

Mp 121–123° C.; MS(APCI/M+)=467.3

EXAMPLE 4

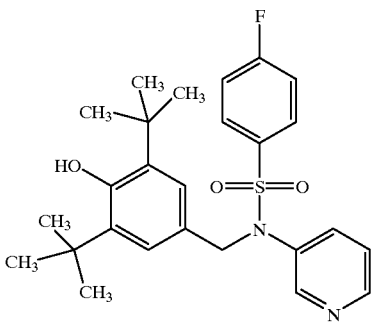

N-(3,5-Di-tert-butyl-4-hydroxy-benzyl)-4-fluoro-N-pyridin-3-yl-benzenesulfonamide The procedure for Example 7 was followed using 4-fluorobenzenesulfonyl chloride. The reaction was heated to 60° C. for 2 hours then stirred at room temperature for 2 days. The residue, after work-up, was chromatographed on silica gel eluting with 40% EtOAc/hexanes and recrystallized from EtOAc/hexanes to obtain desired compound (53%).

Mp 137–138° C.; MS(APCI/M+)=471.2

EXAMPLE 5

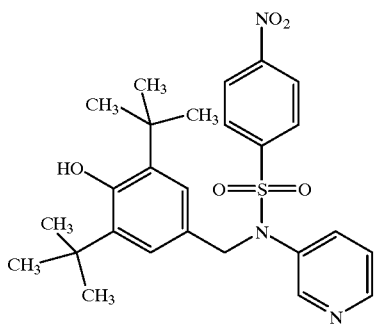

N-(3,5-Di-tert-butyl-4-hydroxy-benzyl)-4-nitro-N-pyridin-3-yl-benzenesulfonamide The procedure for Example 7 was followed using 4-nitrobenzenesulfonyl chloride. The reaction was heated to 60° C. for 2 hours, then stirred at room temperature for 2 days. The residue, after work-up, was chromatographed on silica gel eluting with 40% EtOAc/hexanes and recrystallized to give the desired compound (29%).

Mp 159–160° C.; MS(APCI/M+)=498.2

EXAMPLE 6

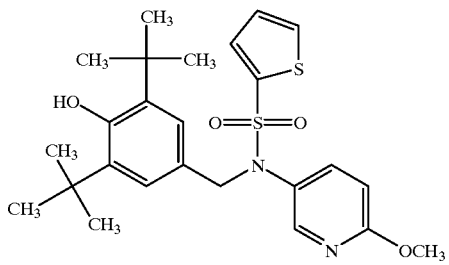

Thiophene-2-sulfonic acid (3,5-di-tert-butyl-4-hydroxy-benzyl)-6-methoxy-pyridin-3-yl-amide The procedure for Example 7 was followed using 2-methoxy-5-aminopyridine in place of 3-aminopyridine. Molecular sieves were added to remove the water generated. After hydrogenation, the crude intermediate was chromatographed on silica gel eluting with 5:1 hexane/EtOAc. The crude sulfonamide was chromatographed on silica gel eluting with 9:1 hex/EtOAc, triturated with hexanes to give the desired product.

Mp: 96–97° C. MS (APCI/M+).

EXAMPLE 7

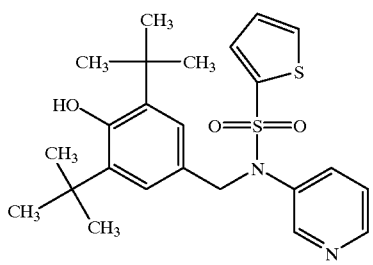

Thiophene-2-sulfonic acid (3,5-di-tert-butyl-4-hydroxy-benzyl)-pyridin-3-yl-amide p-Toluene sulfonic acid (250 mg) was added as a catalyst to a mixture of 3,5-di-t-butuyl-4-hydroxybenzylaldehyde (46.8 g, 200 mmol) and 3-aminopyridine (18.8 g, 210 mmol) in toluene (400 mL). The mixture was refluxed for 20 hours with a Dean-Stark apparatus to remove the water generated. The mixture was cooled, filtered, and concentrated to dryness; the residue was then recrystallized from EtOAc/hexanes yielding 55 g of product.

The product from above was hydrogenated with Raney/Ni in methanol at 40° C. for 20 hours. The solvent was evaporated, and the residue was triturated with small amount of MeOH, the white precipitate collect weight 42 g (71%).

Next, the white precipitate (18.72 gm, 60 mmol), 2-thiophenesulfonyl chloride (12.056 g, 66 mmol) and catalytic amount of DMAP (40 mg) were mixed in pyridine (200 mL) and stirred at 60° C. for 2 days. Pyridine was evaporated, and the residue was distributed in EtOAc (300 mL) and water (500 mL). The organic layer was washed a couple of times with water. The EtOAc layer was dried and evaporated to dryness. The residue was triturated with 100 mL (hexane/EtOAc), and the pale yellow precipitate that was collected weighed 22 g (80%).

Mp 118–120° C.; MS (APCI/M+)=459.1

EXAMPLE 8

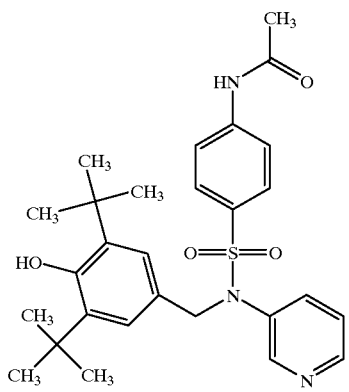

N-(3,5-Di-tert-butyl-4-hydroxy-benzyl)-4-acetamido-N-pyridin-3-yl-benzenesulfonamide The procedure for Example 7 was followed using 4-acetylsulfanilyl chloride. The reaction was stirred at room temperature for 2 days. The residue, after work-up, was chromatographed eluting with 75% EtOAc/hexanes. The product was triturated with heptane and then evaporated to obtain desired compound (42%).

Mp 167–169° C.; MS(APCI/M+)=510.2

EXAMPLE 9

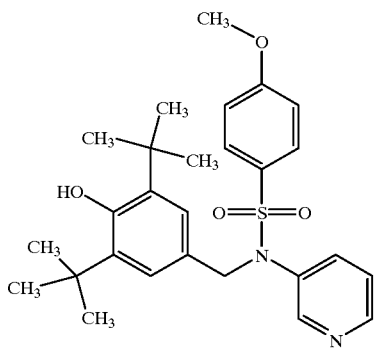

N-(3,5-Di-tert-butyl-4-hydroxy-benzyl)-4-methoxy-N-pyridin-3-yl-benzenesulfonamide The procedure for Example 7 was followed using 4-methoxybenzenesulfonyl chloride. The reaction was heated to 60° C. for 19 hours. The residue, after work-up, was chromatographed on silica gel eluting with 50% EtOAc/hexanes and was recrystallized from EtOAc/hexanes to obtain the desired compound (22%).

Mp 142–143° C.; MS(APCI/M+)=483.2

EXAMPLE 10

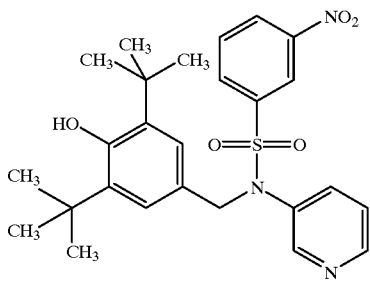

N-(3,5-Di-tert-butyl-4-hydroxy-benzyl)-3-nitro-N-pyridin-3-yl-benzenesulfonamide The procedure for Example 7 was followed using 3-nitrobenzenesulfonyl chloride. The reaction was heated to 60° C. for 17 hours and then stirred at room temperature for 4 days. The residue, after work-up, was chromatographed on silica gel eluting with 50% EtOAc/hexanes, placed on high vacuum and then triturated with hexanes to give the desired compound (8%).

Mp 99–107° C.; MS(APCI/M+)=498.1

EXAMPLE 11

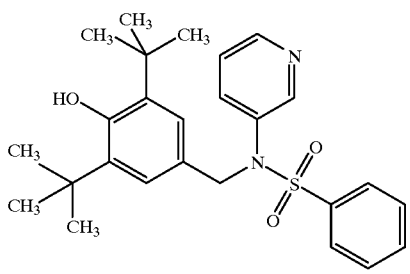

N-(3,5-Di-tert-butyl-4-hydroxy-benzyl)-3-N-pyridin-3-yl-benzenesulfonamide

This compound was prepared in the same manner as for the title compound of Example 7, except the 2-thiophene sulfonyl chloride was replaced with benzene sulfonyl chloride.

Mp 143–145° C.; MS+1=453.3

EXAMPLE 12

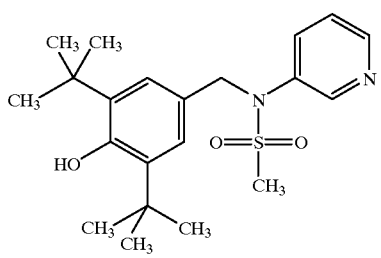

N-(3,5-Di-tert-butyl-4-hydroxy-benzyl)-N-pyridin-3-yl-methanesulfonamide

This compound was prepared in the same manner as for the title compound of Example 7, except the 2-thiophene sulfonyl chloride was replaced with methane sulfonyl chloride.

Mp 133–134° C.; MS+1=391.1

EXAMPLE 13

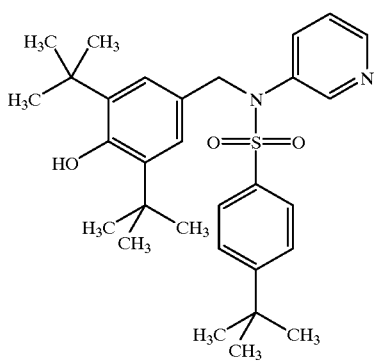

N-(3,5-Di-tert-butyl-4-hydroxy-benzyl)-4-tert-butyl-N-pyridin-3-yl-benzenesulfonamide The procedure for Example 7 was followed using 4-tert-butylbenzenesulfonyl chloride. The reaction was heated to 60° C. for 24 hours. The residue, after work-up, was chromatographed on silica gel eluting with 25% EtOAc/hexanes then recrystallized from EtOAc/hexanes to give the desired compound (4%).

Mp 155–156° C.; MS (APCI/M+)=509.3

EXAMPLE 14

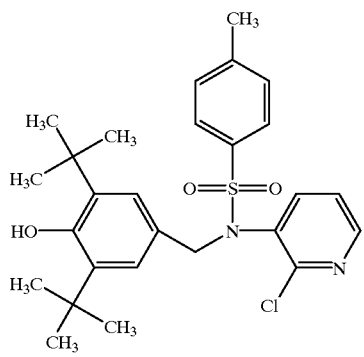

N-(2-Chloro-pyridin-3-yl)-N-(3,5-di-tert-butyl-4-hydroxy-benzyl)-4-methyl-benzenesulfonamide The procedure for Example 7 was followed using 2,6-di-tert-butyl-4-(2-chloropyridin-3-yl aminomethyl) phenol and p-toluenesulfonyl chloride. The reaction was heated to 60° C. for 41 hours. The crude residue was chromatographed on silica eluting with 20% to 25% EtOAc/hexanes and recrystallized from EtOAc/hexanes to give pale yellow crystals (5%).

Mp 117–119° C.; MS(APCI/M+): 501.2

EXAMPLE 15

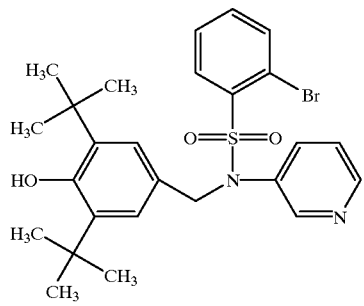

N-(3,5-di-tert-butyl-4-hydroxybenzyl)-2-bromo-N-pyridin-3-yl-benzenesulfonamide

The procedure for Example 7 was followed using 2-bromobenzene sufonyl chloride. The reaction was heated to 60° C. overnight. The crude residue was dissolved in $CH_2Cl_2$ and filtered to remove insoluble particles and then chromatographed on silica eluting with a gradient of EtOAc/hex. The product was recrystallized from EtOAc/hexanes and dried in a 40° C. vacuum oven overnight to give a white fluffy solid (18%).

Mp 105–107° C.; MS (APCI/M+): 531.1/533.1

EXAMPLE 16

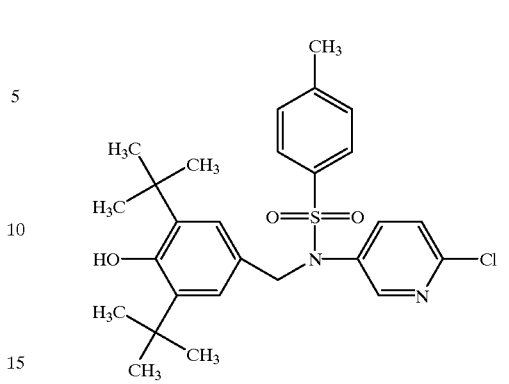

N-(6-Chloro-pyridin-3-yl)-N-(3,5-di-tert-butyl4-hydroxybenzyl)-4-methyl-benzenesulfonamide The procedure for Example 7 was followed using 2,6-di-tert-butyl-4-(4-chloropyridin-3-yl aminomethyl)-phenol and p-toluenesulfonyl chloride. The crude product was chromatographed on silica eluting with 25% EtOAc/hexanes and recrystallized from EtOAc/hexanes to give a white crystals (7.6%).

Mp 152–153° C.; MS(APCI/M+): 501.0

EXAMPLE 17

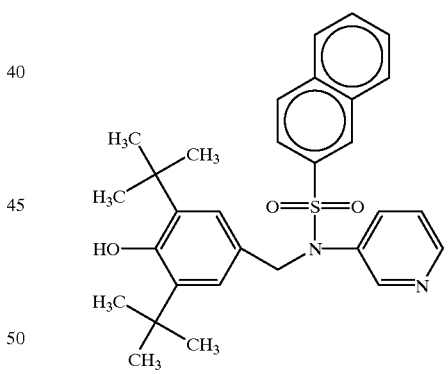

N-(3,5-di-tert-butyl-4-hydroxybenzyl)-2-naphthalene-N-pyridin-3-yl-sulfonamide

The procedure for Example 7 was followed using 2-naphthalenesulfonyl chloride. The crude product was chromatographed on silica eluting with 40% EtOAc/hexanes and recrystallized from EtOAc/hexanes to obtain a white, powdery solid (18%).

Mp 160–171° C.; MS(APCI/M+): 503.2

EXAMPLE 18

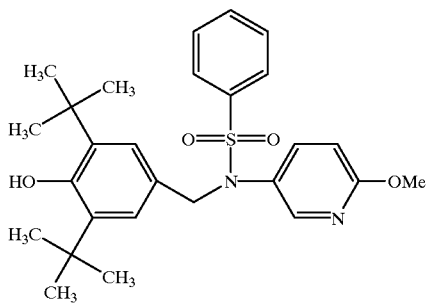

N-(3,5-di-tert-butyl-4-hydroxy-benzyl)-N-(6-methoxy-pyridin-3-yl)-4-methyl-benzenesulfonamide The procedure for Example 7 was followed using 3,5-di-tert-butyl4-(4-methoxy-pyridin-3-yl-aminomethyl) phenol. The reaction was heated to 60° C. for 41.5 hours. The crude product was chromatographed on silica eluting with 20% EtOAc/hexanes and recrystallized from EtOAc/hexanes to obtain an off-white solid (13%).

Mp 127–129° C.; MS(APCI/M+): 497.2

EXAMPLE 19

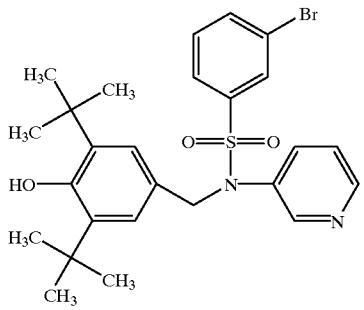

N-(3,5-di-tert-butyl4-hydroxybenzyl)-3-bromo-N-pyridin-3-yl-benzenesulfonamide

The procedure for Example 7 was followed using 3-bromobenzenesufonyl chloride. The reaction was heated to 60° C. overnight. The crude product was chromatographed on silica eluting with a gradient of EtOAc/hexanes. The product was recrystallized from EtOAc/hexanes to give a tan solid (7.3%).

Mp 129–131° C.; MS(APCI/M+): 533.1

BIOLOGICAL METHODS

LPABC Screen

Purpose

The lipoprotein(a), [Lp(a)], biochemical coupling assay (LPABC) is used to characterize inhibitors of the apolipoprotein(a), [apo(a)], apolipoproteinB-100, [apoB-100], coupling reaction that generates Lp(a).

Protocol

Conditioned media from 293 cells (ATCC CRL-1573), permanently transfected with an apo(a) 17-kringle cDNA expression construct (pcDNA-AMP, In Vitrogen, Carlsbad, Calif.) using standard molecular biology techniques, was used as a source of recombinant apo(a) is diluted 1:3 with phosphate buffered saline (PBS) and 90 µL is pipetted into each well of a 96-well plate and placed into 37° C. incubator for 10 minutes. Twenty microliters of a 0.3 to 50 µM solution of a compound of the present invention in PBS is added to the warmed plate. Ninety microliters of HepG2 (ATCC HB-8065) cell conditioned media diluted 1:3 with PBS is added to the apo(a)/compound mixture and mixed by pipetting up and down 5 times. The reaction is incubated for 67 minutes in a 37° C. incubator. A 100 µL aliquot of the reaction is removed and assayed for its Lp(a) content by an enzyme linked immunosorbent assay (ELISA).

LPA3 Screen

Purpose

The LPA3 screen is used to identify compounds that inhibit Lp(a) production. This screen employs permanently transfected HepG2 cells (HepG2$^{K17}$) that are generated using an apo(a) 17-kringle cDNA expression construct (pcDNA-AMP, In Vitrogen, Carlsbad, Calif.) in accordance with methods that are well-known in molecular biology.

Protocol

HepG2$^{K17}$ cells are seeded in 96-well plates at a density of 75,000 cells per well in 0.25 mL of Dulbecco's Modified Eagle Media (DMEM) containing 10% fetal bovine serum (FBS). Seeded plates are incubated overnight in a 37° C., 5% $CO_2$/95% $O_2$ incubator. The media is removed, replaced with (1) fresh media, or (2) fresh media plus 0.3 to 50 µM of a compound of the present invention in 20 µL of PBS, and the plates returned to the incubator for 8 hours. After the additional 8 hours of incubation, Lp(a) is assayed in the media by ELISA. Cells are digested with 0.5N NaOH overnight and assayed for total protein. Lp(a) values are normalized for total protein content.

| Example Number | LPABC IC$_{50}$ µM | LPA3 IC$_{50}$ µM |
|---|---|---|
| 1 | 1.66 | |
| 2 | 1.92[a] | 27.25[a] |
| 3 | 3.94[a] | 6.9 |
| 4 | 2.6 | 7.5 |
| 5 | 2.6 | 9.4 |
| 6 | 3.15 | |
| 7 | 3.5 | 8.9 |
| 8 | 3.5 | 12.5 |
| 9 | 3.7 | 5.8 |
| 10 | 4.0 | 7.4 |
| 11 | 4.12 | 16.2 |
| 12 | 5.58 | 41.2 |
| 13 | 11.8 | 23.6 |
| 14 | 2.1 | |
| 15 | 2.43 | |
| 16 | 2.1 | |
| 17 | 7.1 | |
| 18 | 2.42 | |
| 19 | 2.76 | |

[a]Average of 2 tests

What is claimed is:

1. A compound of the Forrnula I

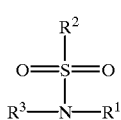

wherein

R¹ is —(CH₂)ₙ-C₃-C₈ cycloalkyl, —(CH₂)ₙ-aryl or —(CH₂)ₙ-aryl substituted by 1 to 3 substituents which are —C₁-C₆ alkyl, —O—C₁-C₆ alkyl, —S—C₁-C₆ alkyl, —OH, —SH, —F, —CN, —Cl, —Br, —I, —CF₃, —NO₂, —CO₂H, —CO₂C₁-C₆ alkyl, —NH₂, —NHC₁-C₆ alkyl, N(C₁-C₆alkyl)₂, or —

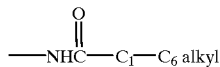

R² is C₁-C₆ alkyl, aryl, aryl substituted by 1 to 3 substituents which are —C₁-C₆ alkyl, —O—C₁-C₆ alkyl, and —S—C₁-C₆ alkyl, —OH, —SH, —F, —CN, —Cl, —Br, —I, —CF₃, —NO₂, —CO₂H, —CO₂C₁-C₆ alkyl, —NH₂, —NHC₁-C₆ alkyl, N(C₁-C₆alkyl)₂, or —NH(O=C)—C₁-C₆ alkyl, or R³ is

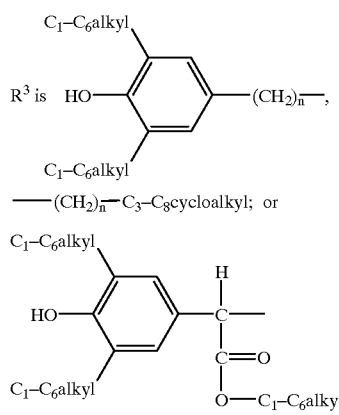

—(CH₂)ₙ-C₃-C₈cycloalkyl; or

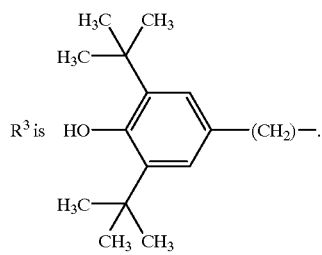

n is 0 to 4, and the pharmaceutically acceptable salts thereof.

2. A compound in accordance with claim 1 wherein

R³ is

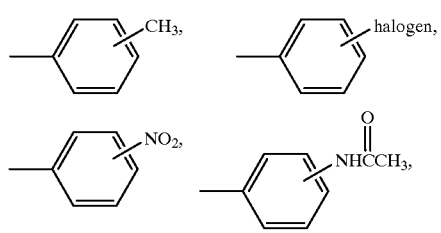

3. A compound in accordance with claim 1 wherein R² is

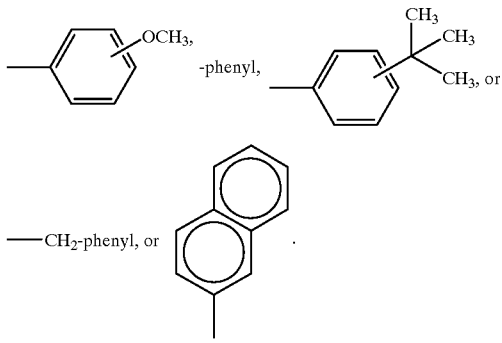

4. A compound in accordance with claim 1 wherein R¹ is —CH₂-cyclohexyl.

5. A compound of the Formula I

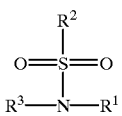

I wherein

R¹ is —CH₂ cyclohexyl;

R² is —C₁-C₆ alkyl, substituted phenyl, or —CH₂-phenyl;

R³ is

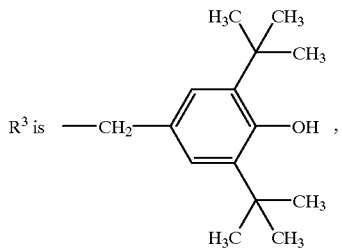

salt thereof.

6. The compound of claim 1 which is (Cyclohexylmethyl-methanesulfonyl-amino)-(3,5-di-tert-butyl-4-hydroxy-phenyl)-acetic acid ethyl ester.

7. A pharmaceutical composition comprising an effective amount of a compound of claim 1 in combination with a pharmaceutically acceptable carrier or diluent.

8. A pharmaceutical composition comprising an effective amount of a compound of claim 5 in combination with a pharmaceutically acceptable carrier or diluent.

9. A method of lowering plasma Lp(a) in a patient, the method comprising administering to a patient in need of Lp(a) lowering, a therapeutically effective amount of a compound of claim 1.

10. A method of lowering plasma Lp(a) in a patient, the method comprising administering to a patient in need of Lp(a) lowering, a therapeutically effective amount of a compound of claim 5.

11. A method of treating atherosclerosis, the method comprising administering to a patient having or at risk of having atherosclerosis, a therapeutically effective amount of a compound of claim 1.

12. A method of treating atherosclerosis, the method comprising administering to a patient having or at risk of having atherosclerosis, a therapeutically effective amount of a compound of claim 5.

13. A method of treating coronary heart disease, the method comprising administering to a patient having coronary heart disease, a therapeutically effective amount of a compound of claim 1.

14. A method of treating coronary heart disease, the method comprising administering to a patient having coronary heart disease, a therapeutically effective amount of a compound of claim 5.

15. A method of treating restenosis, the method comprising administering to a patient having restenosis, a therapeutically effective amount of a compound of claim 1.

16. A method of treating restenosis, the method comprising administering to a patient having restenosis, a therapeutically effective amount of a compound of claim 5.

* * * * *

UNITED STATES PATENT AND TRADEMARK OFFICE
CERTIFICATE OF CORRECTION

PATENT NO.    : 6,284,795 B1
DATED         : September 4, 2001
INVENTOR(S)   : Helen Tsenwhei Lee et al.

It is certified that error appears in the above-identified patent and that said Letters Patent is hereby corrected as shown below:

<u>Column 20,</u>
Line 45, "salt thereof." should read -- or a pharmaceutically acc eptable salt thereof --.

Signed and Sealed this

Twenty-ninth Day of April, 2003

JAMES E. ROGAN
*Director of the United States Patent and Trademark Office*